(12) United States Patent
Coucharriere et al.

(10) Patent No.: US 10,316,005 B2
(45) Date of Patent: Jun. 11, 2019

(54) PROCESS FOR THE PREPARATION OF BIS-DMTD

(75) Inventors: Carole Coucharriere, Carcen Ponson (FR); Thierry Aubert, Pau (FR); Dominique Bonhomme, Capbreton (FR); Jean-Yves Ehlinger, Dax (FR)

(73) Assignee: MLPC INTERNATIONAL, Rion des Landes (FR)

( * ) Notice: Subject to any disclaimer, the term of this patent is extended or adjusted under 35 U.S.C. 154(b) by 471 days.

(21) Appl. No.: 12/828,334

(22) Filed: Jul. 1, 2010

(65) Prior Publication Data
US 2011/0004001 A1    Jan. 6, 2011

(30) Foreign Application Priority Data

Jul. 6, 2009 (FR) ...................................... 09 03323

(51) Int. Cl.
*C07D 285/125*    (2006.01)
*C07D 417/12*    (2006.01)

(52) U.S. Cl.
CPC ................................ *C07D 285/125* (2013.01)

(58) Field of Classification Search
CPC ........................... C07D 285/125; C07D 417/12
See application file for complete search history.

(56) References Cited

U.S. PATENT DOCUMENTS

| | | | | |
|---|---|---|---|---|
| 3,087,932 A | * | 4/1963 | Little, Jr. | ....................... 548/142 |
| 4,599,425 A | * | 7/1986 | Hugo | ................... C07D 513/18 |
| | | | | 548/142 |
| 2006/0168741 A1 | | 8/2006 | Laufer et al. | |

FOREIGN PATENT DOCUMENTS

CN          101096366          1/2008

OTHER PUBLICATIONS

Surfactant, 2012, http://en.wikipedia.org/wiki/Surfactant.*
Processing-Aid, 2018, https://tri-epa.zendesk.com/hc/en-us/articles/211671098-What-is-the-difference-between-a-manufacturing-aid-and-processing-aid-.*

* cited by examiner

*Primary Examiner* — Sun Jae Yoo
(74) *Attorney, Agent, or Firm* — Smith, Gambrell & Russell, LLP

(57) ABSTRACT

The present invention relates to a process for the preparation of bis(dimercaptothiadiazole) (or bis-DMTD), more particularly of 5,5'-dithiobis(1,3,4-thiadiazole-2-thiol), said process being carried out in a single reactor and making possible a preparation with improved yields which is more respectful of the environment.

23 Claims, No Drawings

PROCESS FOR THE PREPARATION OF BIS-DMTD

The present invention relates to an improved process for the preparation of bis(dimercaptothiadiazole) (or bis-DMTD), more particularly of 5,5'-dithiobis(1,3,4-thiadiazole-2-thiol), also known as 5,5'-dithiobis(1,3,4-thiadiazole-2(3H)-thione) in its tautomeric form, said process making possible a preparation with improved yields which is more respectful of the environment.

The preparation of bis-DMTD has been known for many years and is, for example, described in patent application CN-A-101096366.

Thus, the synthesis of bis-DMTD is carried out by oxidation of 2,5-dimercapto-1,3,4-thiadiazole (or DMTD, CAS No. 1072-71-5), for example with hydrogen peroxide, according to the following reaction scheme:

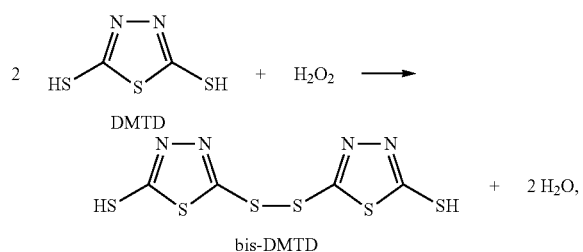

it also being possible for which reaction to be written, revealing the tautomeric forms:

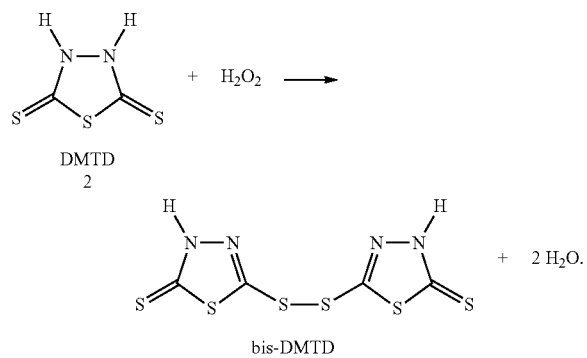

This reaction has formed the subject of a large number of studies, such as, for example, that published in 2006 in patent application US 2006/0168741, showing, inter alia, the difficulty in selectively obtaining bis-DMTD, that is to say while minimizing formation of cyclic dimer or the formation of oligomers, indeed even of polymers.

However, all these studies are based on the use, as starting material, of 2,5-dimercapto-1,3,4-thiadiazole (DMTD).

In point of fact, it is well known that the reaction for the synthesis of DMTD generates aqueous effluents in which a not insignificant amount of DMTD is dissolved. The solubility in water of DMTD is from approximately 8 g/l to 30 g/l, according to the temperature and pH conditions, which results in a loss in yield but also and especially in an expensive treatment of the effluents in order to reduce their very high content of oxidizable organic matter, measured by the Chemical Oxygen Demand (COD), which is generally in the order of 15 g/l to 60 g/l approximately.

This is because the synthesis of DMTD is generally carried out starting from hydrazine and carbon disulfide in aqueous solution, according to the following reaction scheme:

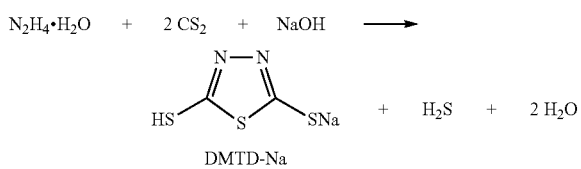

the sodium salt of DMTD (DMTD-Na) being subsequently acidified to give DMTD by means of an acidic aqueous solution, for example sulfuric acid in aqueous solution.

There thus today remains a need relating to a process for the preparation of bis-DMTD which is selective and more respectful of the environment, in comparison with existing processes.

Thus, a first object of the present invention is to provide a process for the synthesis of bis-DMTD which is as selective as possible, with the highest possible yields.

Another object of the present invention is to provide a process for the synthesis of bis-DMTD which is as respectful as possible of the environment, in particular a synthesis process where the effluents generated have a smaller load of organic products, consequently requiring treatments of said effluents with lower costs.

The Applicant Company has now discovered a process which makes it possible to achieve, in all or at least in part, the abovementioned objects by virtue of the process of the invention which is described in detail in the continuation of the present account.

The invention relates to a process for the preparation of bis-DMDT in which the synthesis intermediate DMTD, obtained as suspension in water (with a solubility from approximately 8 g/l to 30 g/l, according to the temperature and pH conditions, as indicated above), is not isolated, which thus does not generate aqueous effluents with a high load of DMTD, the generator of high COD.

The process of the invention is thus carried out in just one reactor (one-pot reaction) by introduction of the starting materials (hydrazine and carbon disulfide) and recovery of the final product, bis-DMTD.

Surprisingly, in comparison with the state of the art, where the one-pot synthesis is not favored, the process according to the present invention, without isolation of the intermediate DMTD, results in bis-DMTD being obtained with good yields and a high selectivity. In addition, the final product obtained is of high purity, which is rarely the case in such one-pot syntheses, where the impurities generated in the first stages are not removed.

More specifically, the present invention relates to a process for the preparation of bis-DMTD comprising at least the following reaction stages:
a) reaction of hydrazine $N_2H_4$ with carbon disulfide $CS_2$ in a basic medium;
b) acidification of the reaction medium;
c) oxidation of the reaction medium;
d) recovery and optional purification of the bis-DMTD formed.

Stage a) is carried out in an aqueous phase, for example in water. The use of an aqueous/organic phase can be envisaged but is not preferred due to the difficulties in treating these aqueous/organic and organic effluents at the end of the reaction and their impact on the environment.

The hydrazine used can be of any type and it is preferable to use hydrazine monohydrate $N_2H_4.H_2O$. Likewise, there exists no particular recommendation with regard to the nature of the carbon disulfide $CS_2$ used, apart from the usual operating precautions related to the use of this product.

According to a preferred embodiment, the starting materials used in the process of the present invention comprise a content of dissolved metals which is as low as possible, indeed even are devoid of dissolved metals. According to a more particularly preferred embodiment, the contents of dissolved metals in the starting materials are less than 300 ppm, advantageously less than 200 ppm and very advantageously less than 100 ppm.

The carbon disulfide/hydrazine ($CS_2/N_2H_4$) molar ratio can vary within wide proportions and is advantageously between 1.8 and 4.0, preferably between 2.0 and 3.0, more preferably between 2.0 and 2.5 and entirely preferably between approximately 2.2 and 2.4.

This first stage of reaction between hydrazine and carbon disulfide is carried out in a basic medium, for example in the presence of a strong inorganic or organic base, preferably a strong inorganic base. More preferably, the inorganic base is an alkali metal or alkaline earth metal hydroxide, sodium hydroxide being preferred, in particular because of its low cost.

The amount of base in the reaction medium can also vary within wide proportions. Generally, the base/hydrazine molar ratio is between 0.8 and 1.5, preferably between 1.0 and 1.2 approximately.

According to a preferred aspect, the carbon disulfide is slowly added to the basic aqueous hydrazine solution at a temperature of between 20° C. and 45° C., preferably, for example, in the vicinity of 40° C.

After addition of the carbon disulfide, the reaction temperature can be adjusted according in particular to the desired reaction kinetics. Thus, the reaction temperature can be set at a value of between 0° C. and 100° C., for example in the vicinity of 98° C.

This first stage is generally carried out at atmospheric pressure but it is not ruled out to operate under pressure or also under slight vacuum. Particularly advantageously, this step, and also the entire process, is carried out under an inert atmosphere, for example under nitrogen.

The reaction between hydrazine and carbon disulfide results in the formation of a DMTD salt, which is not isolated, with release of hydrogen sulfide, which can advantageously be trapped, according to any method known to a person skilled in the art, for example in a trap containing an aqueous sodium hydroxide solution.

After cooling the reaction medium resulting from stage a), the DMTD salt is acidified, in the same synthesis reactor, to give DMTD.

This acidification stage b) is carried out under the action of an acid, generally a strong acid, which is inorganic or organic, preferably inorganic, such as, for example, sulfuric acid, nitric acid or hydrochloric acid, preferably sulfuric acid.

Use will preferably be made of a solution of acid in water in carrying out this stage. The concentration of acid can vary within wide proportions, according to the nature of the base used in stage a) and according to the pH of the reaction medium.

Preferably, the amount of acid added to the reaction medium is such that the pH of the medium is less than 5, preferably less than 4, more specifically between 0 and 4.

According to an alternative form, the amount of acid added is necessary and sufficient to acidify the reaction medium while keeping the DMTD formed in the DMTD monosalt form, comprising a free —SH functional group and an —SX functional group, where X represents the counterion of the base used in stage a), as illustrated by the following formula:

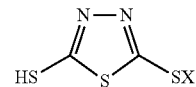

By way of example, when the base used in stage a) is sodium hydroxide, X represents the sodium atom Na. The use of the above monosalt in stage c) of oxidation to give bis-DMTD defined below exhibits the advantages described in patent application US 2006/0168741, making it possible to improve the selectivity for formation of DMTD dimer while reducing the risks of formation of higher polymers and of cyclic dimers.

Stage b) is generally carried out at ambient temperature and it may be necessary, but not compulsory, to cool the reaction medium in order to keep the temperature in the vicinity of ambient temperature during the addition of the acid solution.

On conclusion of this acidification stage, the reaction medium, comprising mainly DMTD predominantly in suspension in the water and a part in solution in the water, is used, still in the same reactor, without isolation or drying of the intermediate DMTD, in stage c) of oxidation of the DMTD to give bis-DMTD.

To do this, an amount of an oxidizing agent which can be of any type generally used in the field, for example chosen from peroxides, such as hydrogen peroxide (aqueous hydrogen peroxide solution), organic or inorganic peracids, in particular peracetic acid, and mixtures between them or with strong acids, for example hydrogen peroxide/strong acids mixtures where the strong acid may be sulfuric acid or hydrochloric acid, is added to the reaction medium.

It is preferable to use hydrogen peroxide as oxidizing agent. The use of peracetic acid releases, after the reaction, acetic acid into the effluents, then increasing the COD load. However, this COD load due to the presence of acetic acid can be easily lowered by conventional treatment of the effluents (for example treatment plant). This treatment of effluents loaded with acetic acid is, of course, much easier than the treatment of the effluents loaded with DMTD observed with the known conventional processes of the prior art.

The oxidizing agent preferred for the process of the present invention is aqueous hydrogen peroxide solution (hydrogen peroxide) at a concentration of between 30 and 70% by weight, for example approximately 35% by weight.

The oxidizing agent/DMTD molar ratio is generally between 0.35:1 and 0.65:1; preferably the molar ratio is between 0.45:1 and 0.55:1. A molar ratio below 0.45:1 may be insufficient to provide the completest possible conversion of DMTD to give bis-DMTD without generating by-products, whereas a molar ratio above 0.55:1 can result in the formation of undesired by-products, such as products from the polymerization of DMTD.

For the oxidation stage, the oxidizing agent is added to the reaction medium resulting from stage b) and the oxidation reaction is carried out at a temperature generally of between 10° C. and 100° C., preferably between 35° C. and 65° C. and very particularly preferably between 50° C. and 55° C.

As for the preceding stages, the oxidation stage is preferably and advantageously carried out at atmospheric pressure, preferably under an inert atmosphere.

The bis-DMTD formed exists in the form of fine particles. It can also be advantageous to add, to the reaction medium, during or after the oxidation reaction, a processing aid which makes possible easier recovery of the bis-DMTD precipitate by making it possible to limit the pulverulent nature of the final powder and thus to facilitate the use thereof.

The processing aids can be of any type and are well known to the person skilled in the art. Particularly appropriate processing aids are, for example, oils, advantageously of naphthenic or paraffinic oil type, in particular the oil "85 Neutral Solvent" from Total.

The amount of processing aid can vary within wide proportions and a person skilled in the art will know how to adjust this amount to the specific requirements resulting from the synthesis carried out. As a general rule, the amount of processing aid is between 0.01 and 10% by weight, with respect to the expected weight of bis-DMTD formed; preferably, in particular when the processing aid is an oil as indicated above, the amount by weight added is between 0.1 and 5% of the expected weight of bis-DMTD, more preferably between 1 and 3%.

The process according to the present invention can advantageously be carried out in the presence of at least one surfactant, preferably nonionic surfactant, such as, for example, Tergitol™ 15-S-5 from Dow Chemicals.

The amount of surfactant is generally between 0.01% by weight and 10% by weight, preferably between 0.1 and 5%, more preferably between 0.1 and 1%, of the expected weight of bis-DMTD.

The final product expected, in the form of a precipitate in the reaction medium, which is an aqueous phase, indeed even an aqueous/organic phase, is thus recovered according to conventional methods known in the field, for example chosen from one or more of the following operations: separation by settling, filtration, centrifuging, draining, pressing and others.

The bis-DMTD obtained in the solid form can subsequently be washed, advantageously with water, in particular with the aim of removing water-soluble impurities, such as sulfates and hydrogensulfates. The bis-DMTD can, if desired or if necessary, be purified according to any conventional purification method known to a person skilled in the art, for example by recrystallization from one or more appropriate solvents.

Finally, the bis-DMTD is advantageously dried, for example under vacuum or under a stream of air, optionally in combination with a temperature advantageously of between 50° C. and 150° C., preferably between 60° C. and 110° C. and more preferably between 70° C. and 90° C., before optional packaging, in particular for the storage and transportation of the finished product.

The process of the present invention exhibits the advantage of involving, in the oxidation reaction, both solid DMTD in suspension and DMTD soluble in the water, with a virtually complete degree of conversion of the DMTD, without discharge or only with very small amounts of DMTD discharged in the effluents resulting from the reaction.

Furthermore, as bis-DMTD is virtually insoluble in water, the effluents thus generated during the process of the invention, including the aqueous mother liquors resulting from the recovery, comprise neither DMTD nor bis-DMTD, or only traces of these products. The result of this is that the amount of organic matter in these effluents (COD) is very low, generally less than 10 g/l, more generally less than 5 g/l, indeed even less than 2 g/l, in contrast to the conventional processes carried out in two stages, the COD content of which in the effluents generally amounts to values of greater than 15 g/l.

The chemical oxygen demand (COD) of the water is defined as being the weight by volume of oxygen equivalent to the weight of sodium dichromate consumed under given operational conditions for the oxidation of the oxidizable matter in the water. The measurement of the COD can be carried out according to any method known to a person skilled in the art, in particular according to the method of reference ISO 15705:2002.

The process of the invention thus makes it possible to avoid the discharge of effluents loaded with DMTD and, consequently, a loss of the synthesis intermediate. This results in not insignificant increases in yield with respect to the syntheses of the prior art, all the DMTD formed as intermediate being used in the oxidation reaction resulting in the bis-DMTD.

Thus, according to the concentrations of the reaction medium which are employed, increases in yield, based on the number of moles of bis-DMTD formed with respect to the number of moles of hydrazine involved at the start, are of the order of 5 to 10%, and even greater.

The process according to the present invention is consequently entirely suitable for industrial production, this being all the more the case as said one-pot process makes it possible to obtain bis-DMTD with a high purity, generally of greater than 96%, more generally of greater than 98%, indeed even of greater than 99%.

The bis-DMTD prepared according to the process of the invention has applications in many fields, in particular due to its antiwear properties and its good resistance to high temperatures and pressures.

Thus, bis-DMTD can advantageously be used as antiwear agent in lubricants, for example for engine oils, heat-transfer fluids or metalworking oils, and more generally in any type of oil liable to be subject to high temperatures and/or pressures.

Bis-DMTD also exhibits antioxidant properties and can thus be used in a large number of applications, such as, for example, those defined above but also coatings, in particular paints, lacquers, varnishes and other film-forming products, in particular aqueous-based ones, especially for the coating of metal parts (construction, door and window frames, hardware, ironwork), and in the production of electrochemical devices, such as batteries (rechargeable chemical batteries, fuel cells and others), accumulators, capacitors, electrolysis cells or electroplating cells, to mention only some among them and without introducing the slightest limitation.

The present invention is now illustrated by means of the example which follows and which does not exhibit any limiting purpose from the viewpoint of the scope of the present invention, the scope furthermore defined by the appended claims.

Example of the Synthesis of Bis-DMTD:

Stage a)

4000 liters of water, 800 kg of hydrazine monohydrate and 1300 kg of a 50% by weight aqueous sodium hydroxide solution are added to a 16 $m^3$ enameled reactor or a reactor made of stainless steel which has been rendered inert beforehand with nitrogen and which is provided with a stirring system. The temperature rises to approximately 30° C.

2900 kg of carbon disulfide are subsequently added over approximately 10 hours at a temperature of between 36° C. and 40° C. The hydrogen sulfide released during the reaction is trapped by absorption/reaction in an aqueous sodium hydroxide solution.

The reaction medium is gradually heated to approximately 98° C. and stripping with nitrogen is carried out at this temperature for 5 hours. The reaction medium is subsequently cooled to 20° C. and then 2000 l of water are added.

Stage b)

2200 kg of 42% sulfuric acid are added, still with stirring and under nitrogen, while maintaining the temperature at 20° C.

Stage c)

770 kg of 35% aqueous hydrogen peroxide ($H_2O_2$) are then added while maintaining the temperature between 50° C. and 55° C., and then stirring is maintained at 50° C. for 2 hours.

Stage d)

36 kg of 85 Neutral Solvent oil from Total are then added and then the product is filtered off on a centrifuge; the product is washed with water and then dried under vacuum at 70° C. 2240 kg of bis-DMTD are recovered, which product has a melting point of 162-164° C. and a purity of 98% (yield=92%).

The COD (chemical oxygen demand) of the aqueous mother liquors is measured with a DR/5000 spectrophotometer (Hach-Lange), after filtration of the bis-DMTD. The COD measured is less than or equal to 5 g/l.

The low toxicity of the effluents generated by the process of the present invention and the good yields observed render said process entirely appropriate for manufacture of bis-DMTD at the industrial level.

What is claimed is:

1. A process for the preparation of bis-DMTD solids, which comprises conducting, in a single reaction vessel without isolation of DMTD, at least the following stages:
    a) reaction of hydrazine ($N_2H_4$) with carbon disulfide ($CS_2$) in a basic medium forming a DMTD salt containing reaction medium;
    b) acidification of the reaction medium containing the DMTD salt to result in DMTD in the reaction medium; and
    c) oxidation of the reaction medium containing the DMTD from step b) with an oxidizing agent and without isolating the DMTD from the reaction medium, and then;
    d) recovering the bis-DMTD solids from the single reaction vessel forming aqueous reaction effluents and optionally purifying the recovered bis-DMTD solids, and
    wherein the formed reaction effluents have a low organic matter load as measured by a Chemical Oxygen Demand (COD) value of less than 10 g/l and wherein the acidification stage is carried out under the action of sulfuric acid.

2. The process as claimed in claim 1, wherein the $CS_2$/$N_2H_4$ molar ratio is between 1.8 and 4.0.

3. The process as claimed in claim 1, wherein stage a) is carried out in an aqueous phase.

4. The process as claimed in claim 1, wherein the basic medium has a base/hydrazine molar ratio is between 0.8 and 1.5.

5. The process as claimed in claim 1, wherein stage a) is carried out in the presence of a surfactant.

6. The process as claimed in claim 1, wherein the oxidation stage c) is carried out by addition of an oxidizing agent to the reaction medium, said oxidizing agent selected from the group consisting of peroxides, organic peracids, inorganic peracids, and mixtures thereof.

7. The process as claimed in claim 1, wherein the oxidizing agent/DMTD molar ratio is between 0.35:1 and 0.65:1.

8. The process as claimed in claim 1, wherein a processing aid is added to the reaction medium during stage d) to limit the pulverlent nature of bis-DMTD and facilitate recovery.

9. The process as claimed in claim 1, wherein the bis-DMTD solids recovered are washed with water and then advantageously dried at a temperature of between 50° C. and 150° C.

10. The process as claimed in claim 1, wherein the amount of organic matter dissolved in the reaction effluents is very low and results in a Chemical Oxygen Demand (COD) value of less than 5 g/l.

11. The process as claimed in claim 1, wherein the $CS_2$/$N_2H_4$ molar ratio is between 2.0 and 3.0.

12. The process as claimed in claim 1, wherein stage a) is carried out in the presence of a strong base, an alkali metal, or alkaline earth metal hydroxide.

13. The process as claimed in claim 5, wherein the surfactant is a nonionic surfactant.

14. The process as claimed in claim 6, wherein the oxidizing agent is combined with one or more strong acids.

15. The process as claimed in claim 14, wherein the strong acid is sulfuric acid or hydrochloric acid and the oxidizing agent is hydrogen peroxide.

16. The process as claimed in claim 8, wherein the processing aid is an oil.

17. The process as claimed in claim 16, wherein the oil is a naphthenic oil, or a paraffinic oil.

18. A process for the preparation of bis-DMTD solids, which comprises conducting, in a single reaction vessel, at least the following stages:
    a) reaction of hydrazine ($N_2H_4$) with carbon disulfide ($CS_2$) in a basic medium forming a DMTD salt containing reaction medium;
    b) acidification of the reaction medium containing the DMTD salt to result in DMTD in the reaction medium; and
    c) oxidation of the reaction medium containing the DMTD from step b) with an oxidizing agent and without isolating the DMTD from the reaction medium, and then;
    d) recovering the bis-DMTD solids from the single reaction vessel forming an aqueous reaction effluent and optionally purifying the recovered bis-DMTD solids,
    wherein stages a)-d) are carried out in the absence of mercaptans, and
    wherein the formed reaction effluents have a low organic load as measured by Chemical Oxygen Demand (COD) value of less than 10 g/l and wherein the acidification stage is carried out under the action of sulfuric acid.

19. The process of claim 1, wherein impurities generated in stage a) are not removed from the single reaction vessel.

20. The process of claim 18, wherein impurities generated in stage a) are not removed from the single reaction vessel.

21. The process of claim 10, wherein the amount of organic matter dissolved in the reaction effluents results in a Chemical Oxygen Demand (COD) value of less than 2 g/l.

22. The process as claimed in claim 1, wherein the oxidizing agent/DMTD molar ratio is between 0.45:1 and 0.55:1.

23. A process for the preparation of bis-DMTD solids, which comprises conducting, in a single reaction vessel without isolation of intermediate DMTD, at least the following stages:
   a) reaction of hydrazine ($N_2H_4$) with carbon disulfide ($CS_2$) in a basic medium forming a DMTD salt containing reaction medium;
   b) acidification of the reaction medium containing the DMTD salt to result in DMTD in the reaction medium; and
   c) oxidation of the reaction medium containing the DMTD from step b) with an oxidizing agent and without isolating the DMTD from the reaction method medium, and then;
   d) recovering the bis-DMTD solids from the single reaction vessel forming aqueous reaction effluents and optionally purifying the recovered bis-DMTD solids, and
wherein the formed reaction effluents have a low organic load as measured by a Chemical Oxygen Demand (COD) value of less than 10 g/l and wherein an oil processing aid is added to the reaction medium during stage d) to limit the pulverlent nature of bis-DMTD and facilitate recovery.

\* \* \* \* \*